(12) United States Patent
Ogawa et al.

(10) Patent No.: US 10,365,255 B2
(45) Date of Patent: Jul. 30, 2019

(54) VIBRATION ANALYSIS DEVICE WHICH CALCULATES CYCLE OF VIBRATION OF TOOL WITH RESPECT TO WORKPIECE

(71) Applicant: FANUC CORPORATION, Minamitsuru-gun, Yamanashi (JP)

(72) Inventors: Hajime Ogawa, Yamanashi (JP); Junichi Tezuka, Yamanashi (JP)

(73) Assignee: FANUC CORPORATION, Yamanashi (JP)

( * ) Notice: Subject to any disclaimer, the term of this patent is extended or adjusted under 35 U.S.C. 154(b) by 367 days.

(21) Appl. No.: 15/258,085

(22) Filed: Sep. 7, 2016

(65) Prior Publication Data
US 2017/0074836 A1   Mar. 16, 2017

(30) Foreign Application Priority Data

Sep. 11, 2015   (JP) ................. 2015-180157

(51) Int. Cl.
*G01H 3/00*       (2006.01)
*G01M 7/00*       (2006.01)
(Continued)

(52) U.S. Cl.
CPC .......... *G01N 29/4454* (2013.01); *G01H 3/00* (2013.01); *G01M 7/00* (2013.01); *G01N 29/04* (2013.01);
(Continued)

(58) Field of Classification Search
CPC .......... B23Q 11/0039; G05B 19/11065; G05B 19/4068; G01N 29/4454; G01N 29/04; G01H 3/00; G01M 7/00
See application file for complete search history.

(56) References Cited

U.S. PATENT DOCUMENTS 4,047,469 A * 9/1977 Sakata ............... B23Q 11/0039
                                                        408/143
4,849,741 A * 7/1989 Thomas ............. G05B 19/4065
                                                        340/683
(Continued)

FOREIGN PATENT DOCUMENTS

JP         2007190628 A       8/2007
JP         2012056051 A       3/2012
(Continued)

OTHER PUBLICATIONS

Notification of Reasons for Refusal for Japanese Application No. 2015-180157, dated Sep. 25, 2017, including English translation, 5 pages.

*Primary Examiner* — Regis J Betsch
*Assistant Examiner* — Kaleria Knox
(74) *Attorney, Agent, or Firm* — RatnerPrestia

(57) ABSTRACT

A vibration analysis device calculates a vibration cycle which occurs during a period in which a workpiece is processed by a machine tool, and includes a tangential velocity calculation unit which calculates a velocity in a tangential direction of a movement path of a processing point by using positional information of a drive axis. The vibration analysis device comprises a movement distance calculation unit which calculates a first movement distance of the processing point on the movement path by using the velocity in the tangential direction. The vibration analysis device comprises a vibration cycle calculation unit which calculates a vibration cycle corresponding to streaks on the basis of previously measured streak intervals on the workpiece and the first movement distance of the processing point.

5 Claims, 10 Drawing Sheets

(51) Int. Cl.
    *G01N 29/04*     (2006.01)
    *G01N 29/12*     (2006.01)
    *G01N 29/44*     (2006.01)

(52) U.S. Cl.
    CPC ......... *G01N 29/12* (2013.01); *G01N 29/4472* (2013.01)

(56) References Cited

U.S. PATENT DOCUMENTS

| | | |
|---|---|---|
| 9,285,797 B2 | 3/2016 | Kondo |
| 9,519,279 B2 | 12/2016 | Tezuka |
| 2013/0096700 A1 | 4/2013 | Tezuka et al. |
| 2014/0244024 A1 | 8/2014 | Tezuka |

FOREIGN PATENT DOCUMENTS

| | | |
|---|---|---|
| JP | 5302371 | 10/2013 |
| JP | 2014008588 A | 1/2014 |
| JP | 2014144522 A | 8/2014 |
| JP | 2014164597 A | 9/2014 |
| JP | 2014220583 A | 11/2014 |

\* cited by examiner

VIBRATION ANALYSIS DEVICE WHICH CALCULATES CYCLE OF VIBRATION OF TOOL WITH RESPECT TO WORKPIECE

BACKGROUND OF THE INVENTION

1. Field of the Invention

The present invention relates to a vibration analysis device which calculates a cycle of vibration of a tool with respect to a workpiece.

2. Description of the Related Art

A machine tool can perform processing while moving at least one of a workpiece (an object to be processed) or a tool along a predetermined drive axis. In other words, a machine tool can perform processing while changing a relative position between a workpiece and a tool. Since the relative position of the tool with respect to the workpiece changes during a processing period, it is preferable for a worker to grasp processing states, such as a velocity of the tool with respect to the workpiece.

Japanese Patent No. 5302371 discloses a numerical control device for a machine tool, which can display physical data of velocities of a drive axis in the machine tool and a representative point of a tool, with reference to a movement distance of the tool. It is disclosed that, in this device, by converting physical data as a function of time into physical data as a function of movement distance, the physical data can be compared at the same processing position even under processing conditions where the velocities and the like are different.

During a period in which a workpiece is processed, a relative position of a tool with respect to the workpiece changes in a state where the tool is in contact with the workpiece. At this time, vibration of a device mounted in the machine tool can be transmitted to a spindle head holding the tool and a table holding the workpiece. Due to this, the workpiece and the tool can vibrate. For example, a fan motor mounted in an inverter or the like can vibrate. Alternatively, vibration can be transmitted from a machine outside the machine tool. When the tool and the workpiece vibrate due to vibration transmitted from such a vibration source, a streak pattern can occur on a processed surface of the workpiece. In other words, streaks can occur at predetermined intervals.

Such a streak pattern is formed depending on a vibration cycle of the tool with respect to the workpiece and a relative velocity of the tool with respect to the workpiece. It is preferable for a worker to be able to also grasp the cycle of vibration which causes occurrence of the streak pattern. However, a machine tool can perform processing while changing the relative velocity of the tool with respect to the workpiece. During a processing period, the velocity of a processing point changes. In this case, the interval between streaks is uneven, and therefore there has been a problem in that it is difficult to calculate the cycle of vibration of the tool with respect to the workpiece.

SUMMARY OF THE INVENTION

A vibration analysis device of the present invention is a vibration analysis device which calculates a vibration cycle at which a tool vibrates with respect to a workpiece during a period in which the workpiece is processed by a machine tool. The vibration analysis device comprises a positional information acquisition unit which acquires positional information of a drive axis in time series. The vibration analysis device comprises a tangential velocity calculation unit which calculates a velocity in a tangential direction of a movement path of a processing point by using the positional information and a movement distance calculation unit which calculates a first movement distance of the processing point on the movement path by using the velocity in the tangential direction. The vibration analysis device includes a streak interval acquisition unit which acquires a previously measured interval between streaks on the workpiece. The vibration analysis device includes a vibration cycle calculation unit which calculates a vibration cycle corresponding to the streaks on the basis of the interval between the streaks and the first movement distance of the processing point.

In the above invention, the vibration cycle calculation unit can calculate a second movement distance of the processing point on the basis of at least two of the intervals between the streaks. The vibration cycle calculation unit can calculate a cross-correlation function of the first movement distance and the second movement distance, and can calculate the vibration cycle corresponding to the streaks on the basis of the cross-correlation function.

In the above invention, the vibration cycle calculation unit can calculate a correlation ratio between the cross-correlation function and an auto-correlation function of the first movement distance. The vibration cycle calculation unit can calculate the vibration cycle at which the correlation ratio is closest to 1, as the vibration cycle corresponding to the streaks.

In the above invention, the vibration cycle calculation unit can calculate a value of a normalized cross-correlation function on the basis of an auto-correlation function of the first movement distance, an auto-correlation function of the second movement distance, and the cross-correlation function. The vibration cycle calculation unit can calculate the vibration cycle at which the value of the normalized cross-correlation function is closest to 1, as the vibration cycle corresponding to the streaks.

In the above invention, the vibration cycle calculation unit can calculate a second movement distance of the processing point on the basis of at least two of the intervals between the streaks. The vibration cycle calculation unit can calculate the vibration cycle at which a difference between the first movement distance and the second movement distance is smallest, as the vibration cycle corresponding to the streaks.

In the above invention, the vibration cycle calculation unit can calculate an integrated value of a square of the difference between the first movement distance and the second movement distance at a plurality of points. The vibration cycle calculation unit can calculate the vibration cycle at which the integrated value is smallest, as the vibration cycle corresponding to the streaks.

DETAILED DESCRIPTION

A vibration analysis device in an embodiment will be described with reference to FIG. 1 to FIG. 17. The vibration analysis device of the present embodiment calculates a vibration cycle at which a tool vibrates with respect to a workpiece during a period in which the workpiece is processed by a machine tool.

Figure 1:
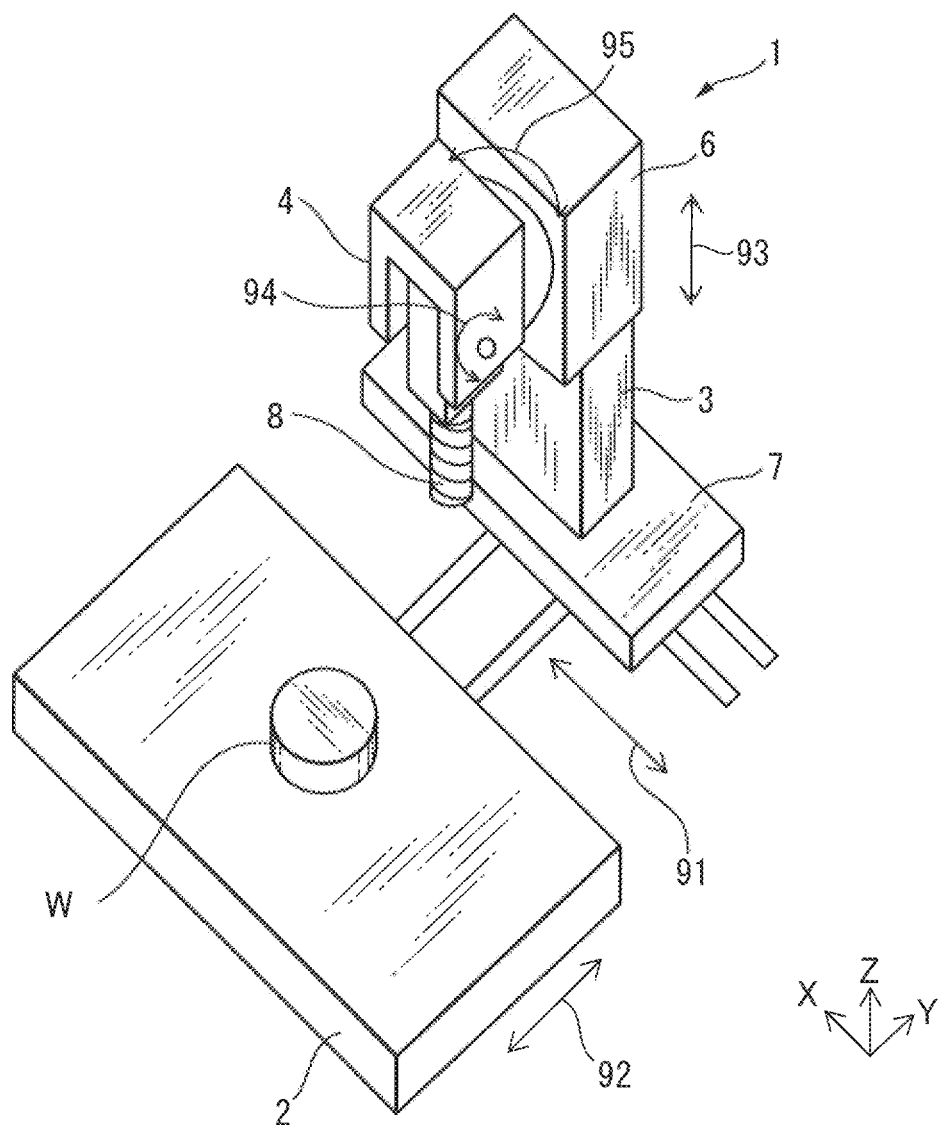
FIG. 1 is a schematic perspective view of a machine tool in an embodiment.

FIG. 1 is a perspective view of a machine tool of the present embodiment. The present embodiment will be described by exemplifying a numerical control type machine tool 1 including five drive axes. The machine tool 1 comprises a table 2 onto which a workpiece W is fixed and a base 7. The machine tool 1 comprises a support column 3 fixed to the base 7. The machine tool 1 comprises a supporting member 6 which moves in a direction indicated by an arrow 93 with respect to the support column 3 and a head 4 supported by the supporting member 6. A tool 8 is supported by the head 4.

The machine tool 1 includes a drive device which changes a relative position and posture of the tool 8 with respect to the workpiece W. The drive device of the present embodiment moves the base 7 in an X-axis direction indicated by an arrow 91. The drive device moves the table 2 in a Y-axis direction indicated by an arrow 92. The drive device moves the supporting member 6 in a Z-axis direction indicated by the arrow 93. Furthermore, the drive device rotates the tool 8 in an A-axis direction with respect to the head 4 as indicted by an arrow 94. The drive device rotates the head 4 in a B-axis direction with respect to the supporting member 6, as indicated by an arrow 95. The machine tool 1 of the present embodiment is formed so that an axial line of an A axis and an axial line of a B axis as rotation axes intersect.

The drive device in the present embodiment controls the relative position and posture of the tool 8 with respect to the workpiece W by drive axes including the three linear axes (X axis, Y axis, and Z axis) and the two rotation axes (A axis and B axis). Then, the workpiece W is processed while the relative position and posture of the tool 8 with respect to the workpiece W are being changed by the drive device. The drive device is not limited to this form, and any device which are capable of changing the relative position of the tool with respect to a workpiece can be employed.

The tool 8 of the present embodiment is a flat end mill. Processing for cutting the workpiece W by using a flat end mill will be described as an example. The tool 8 is not limited to a flat end mill, and any tool can be employed.

Figure 2:
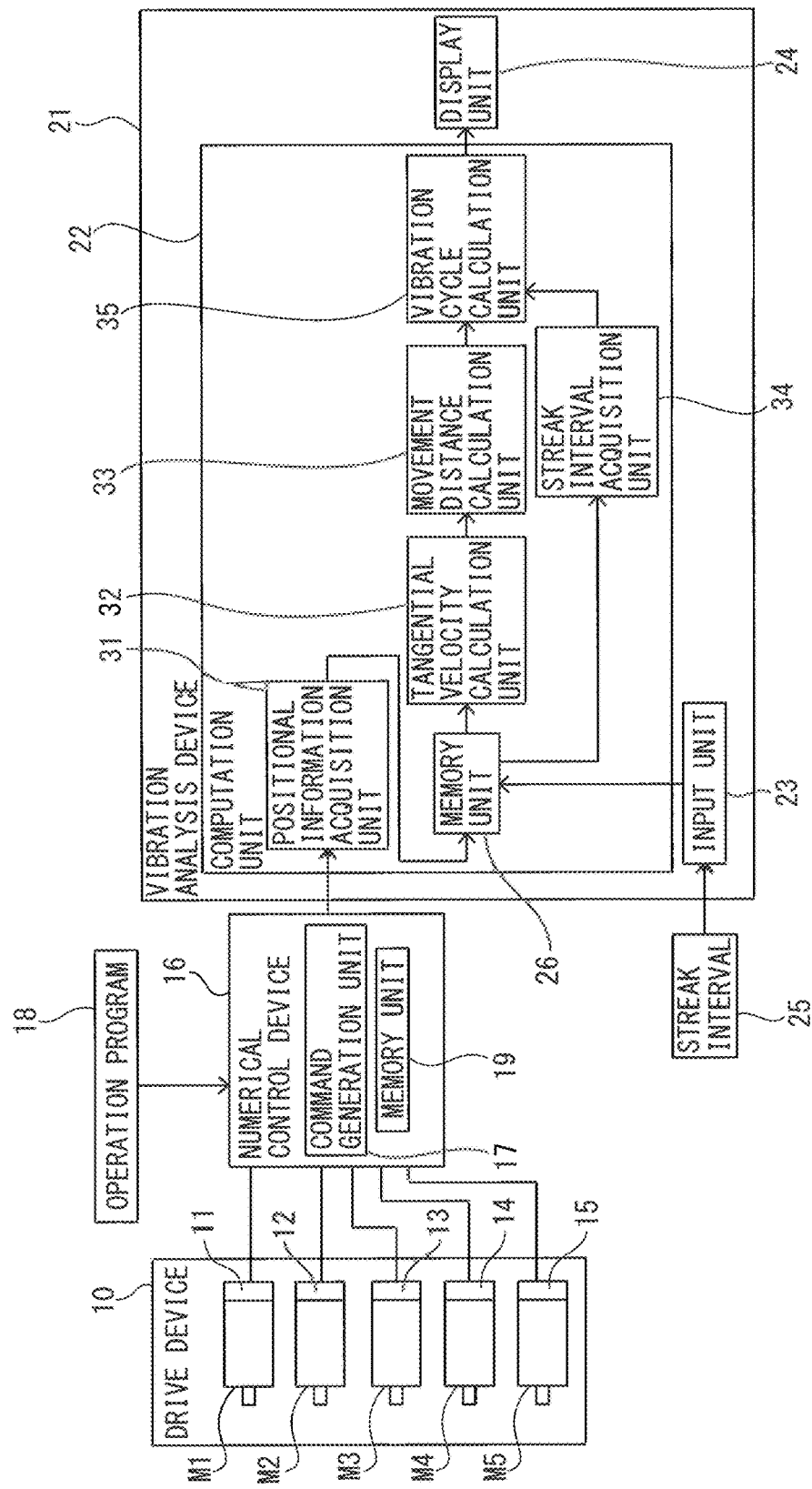
FIG. 2 is a block diagram of the machine tool in the embodiment.

FIG. 2 is a block diagram of the machine tool in the present embodiment. A drive device 10 includes motors M1 to M5 which drive each of the drive axes. The motors M1 to M5 are provided with position detectors 11 to 15 which detect an actual position of each drive axis at each predetermined cycle. The position detectors 11 to 15 of the present embodiment are formed by encoders which are mounted in the motors M1 to M5 and detect rotation angles.

The machine tool 1 comprises a numerical control device 16 which controls the drive device 10 and a vibration analysis device 21 which calculates a cycle of relative vibration of the tool with respect to the workpiece. The vibration analysis device 21 is connected to the numerical control device 16. The vibration analysis device 21 is formed so as to be able to acquire intended information from the numerical control device 16.

The numerical control device 16 is formed by a computation processing device including a CPU (central processing unit), a RAM (random access memory), a ROM (read only memory), and the like connected to one another via bus. Additionally, the numerical control device 16 may include the function of the vibration analysis device 21. In other words, a computation processing device including the functions of the numerical control device 16 and the vibration analysis device 21 may be disposed.

An operation program 18 which operates the machine tool 1 is previously generated by a worker. The numerical control device 16 includes a command generation unit 17 which generates a position command per predetermined control cycle for each drive axis. The command generation unit 17 generates the position command for each drive axis on the basis of the operation program 18 input to the numerical control device 16. The command generation unit 17 calculates a velocity command for each drive axis on the basis of the position command, and furthermore, calculates an electric current command on the basis of the velocity command. Then, the motors M1 to M5 are driven by electric current supplied on the basis of the electric current command.

The numerical control device 16 includes a memory unit 19 which stores information regarding processing of the workpiece W. The memory unit 19 of the present embodiment stores the operation program 18. The command generation unit 17 acquires the operation program 18 from the memory unit 19.

The vibration analysis device 21 includes a computation unit 22, an input unit 23, and a display unit 24. The computation unit 22 is formed by a computation processing device including a CPU, a RAM, a ROM, and the like. The input unit 23 is formed so that the worker can input intended information. Examples of the input unit 23 can include a keyboard and the like. The display unit 24 displays results analyzed by the computation unit 22. The display unit 24 is formed by a display panel or the like.

Figure 3:
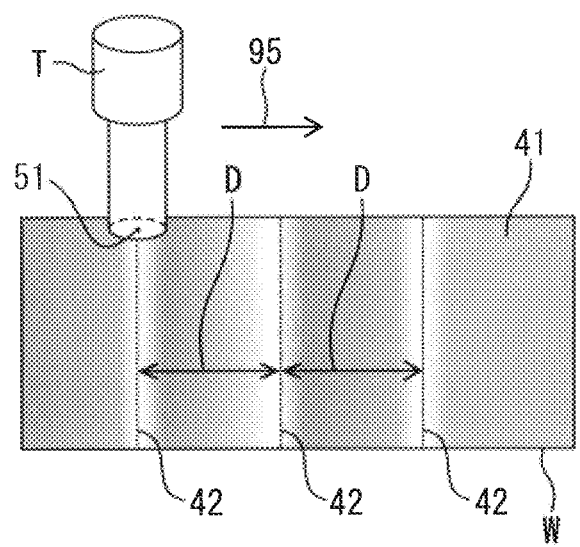
FIG. 3 is a schematic diagram illustrating a streak pattern occurring on the surface of a workpiece.

FIG. 3 shows a schematic diagram of a processed surface of a workpiece after processing. In the present embodiment, a surface 41 of the workpiece W is cut by a bottom portion of the tool 8. In the tool 8, a tool tip point 51 is previously set. In the example of FIG. 3, the tool 8 is moved relatively with respect to the workpiece W in a direction indicated by an arrow 95. When the workpiece W is processed by the machine tool 1, a streak pattern can occur on a processed surface of the workpiece W. The streak pattern occurs when the tool 8 vibrates relatively with respect to the workpiece W. The streak pattern can be visually confirmed, and, in FIG. 3, bright parts and dark parts are alternately formed.

In the present embodiment, the bright parts are referred to as streaks 42 when the workpiece W after processing is seen. In the example shown in FIG. 3, the streaks 42 occur at predetermined intervals D. The streaks 42, for example, extend in a direction intersecting with a direction in which the tool 8 moves relatively with respect to the workpiece W. The streaks 42 occur by transmission of vibration when an optional device mounted in the machine tool 1 is a vibration source. For example, the occurrence is caused by transmission of vibration of a fan motor mounted in an inverter to the head 4 or the table 2. Such a vibration source vibrates at a constant vibration cycle.

Figure 4:
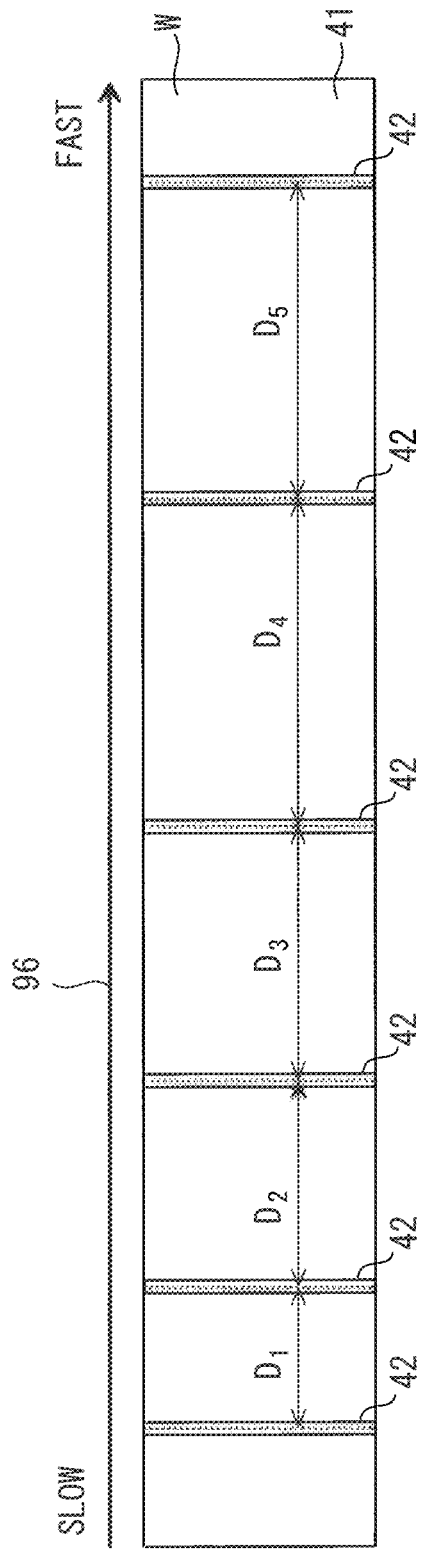
FIG. 4 is a schematic diagram illustrating intervals between streaks occurring on the surface of a workpiece.
Figure 5:
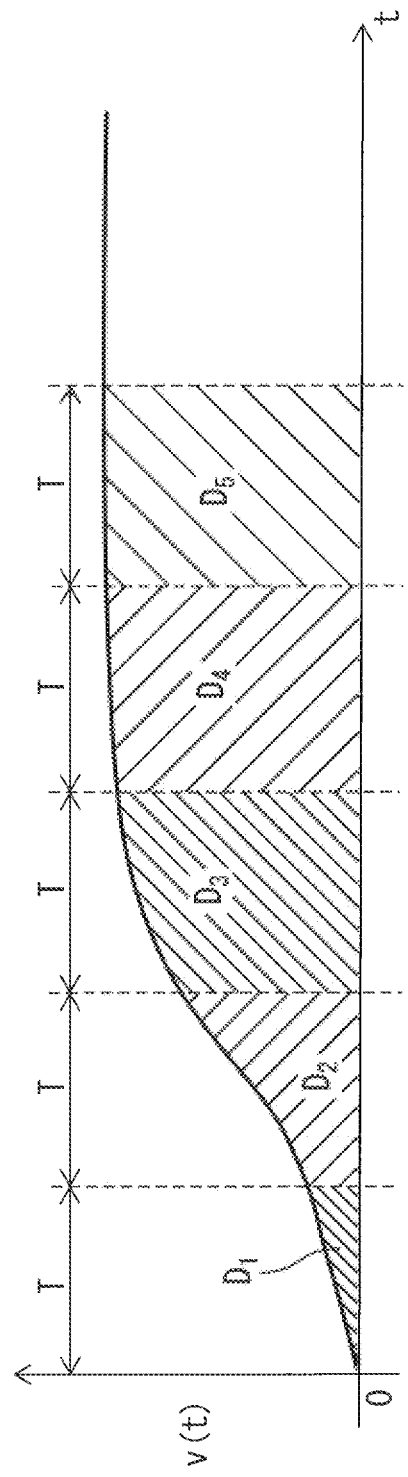
FIG. 5 is a schematic diagram illustrating the velocity of a tool with respect to the workpiece.

FIG. 4 shows a plan view of the workpiece which illustrates streaks occurring on a processed surface of the workpiece. FIG. 5 shows a graph of relative velocity of the tool with respect to the workpiece. Referring to FIG. 4 and FIG. 5, the tool 8 is moved with respect to the workpiece W, as indicated by an arrow 96. Since vibration from a vibration source has a constant vibration cycle T, intervals between the streaks 42 depend on a relative velocity of the tool 8 with respect to the workpiece W.

During a period in which the workpiece W is processed, the relative velocity of the tool with respect to the workpiece W can change. In the examples shown in FIG. 4 and FIG. 5, the velocity of the tool 8 with respect to the workpiece W gradually is larger with the passage of time. In regions with a small velocity, an interval $D_1$ and the like between the streaks 42 are narrow. Then, in regions with a large velocity, an interval $D_5$ and the like between the streaks 42 are larger. In FIG. 5, in the constant vibration cycle T, an area of a region surrounded by the graph and a time axis corresponds to the intervals $D_1$ to $D_5$ between the streaks 42.

The vibration analysis device 21 calculates the vibration cycle T on the basis of intervals between the streaks 42 and positional information at a time when the tool has been moved. The vibration analysis device 21 of the present embodiment can calculate the vibration cycle T even in a region in which the relative velocity of the tool 8 with respect to the workpiece W changes.

First, a first vibration analysis device of the present embodiment will be explained. With reference to FIG. 3, a worker previously measures intervals between the streaks 42 on the workpiece W after processing. Lengths of the intervals between the streaks 42 can be actually measured by a scale or the like. Alternatively, the worker can measure the intervals between the streaks 42 by analyzing a captured image of a surface of the workpiece W. In addition, the intervals between the streaks 42 on the workpiece W can be measured by an arbitrary method.

Referring to FIG. 2, the worker inputs a streak interval 25 by using the input unit 23. The computation unit 22 includes a memory unit 26 which stores information regarding analysis of vibration. The computation unit 22 stores the input streak intervals 25 in the memory unit 26. In addition, the memory unit 26 stores the positional information of each drive axis acquired from the position detectors 11 to 15.

The computation unit 22 includes a streak interval acquisition unit 34. The streak interval acquisition unit 34 acquires the streak intervals input by the worker from the memory unit 26. The computation unit 22 includes a positional information acquisition unit 31, a tangential velocity calculation unit 32, and a movement distance calculation unit 33. The computation unit 22 includes a vibration cycle calculation unit 35 which calculates a vibration cycle corresponding to streaks. The vibration cycle calculation unit 35 calculates a cycle of vibration of the tool with respect to the workpiece on the basis of the intervals between the streaks 42 acquired from the streak interval acquisition unit 34 and a first movement distance of a processing point output from the movement distance calculation unit 33.

Figure 6:
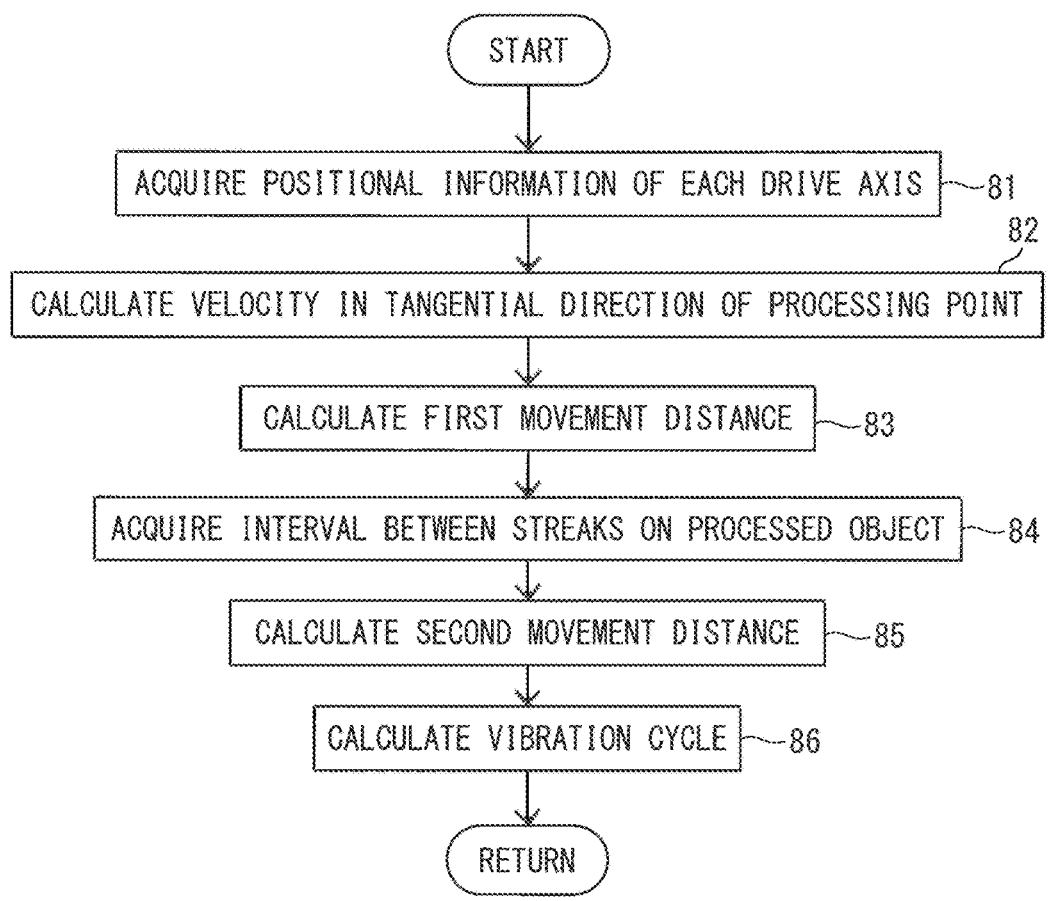
FIG. 6 is a flowchart of control in the embodiment.

FIG. 6 shows a flowchart of control of the vibration analysis device of the present embodiment. At step 81, the positional information acquisition unit 31 acquires positional information of the drive axes together with time points at each previously determined time interval during a period in which the workpiece W is processed. In other words, the positional information acquisition unit 31 acquires the positional information of the drive axes in time series. The positional information acquisition unit 31 of the present embodiment acquires, in time series, the position of each drive axis detected by the position detectors 11 to 15. Alternatively, the positional information acquisition unit 31 may acquire, as time-series data, a position command value of each control cycle generated by the command generation unit 17. The computation unit 22 stores the acquired positional information in the memory unit 26.

At step 82, the tangential velocity calculation unit 32 calculates coordinate values of the tool tip point 51 of the tool 8 on the basis of the positional information and a configuration of the machine tool 1. The configuration of the machine tool 1 includes information on configurations of the drive axes and information on the kind and size of the tool 8. The configuration of the machine tool 1 is previously input to the computation unit 22 and stored in the memory unit 26. The tangential velocity calculation unit 32 calculates time-series coordinate values of the tool tip point 51 in a manner corresponding to time-series positional information.

In the machine tool 1 of the present embodiment, a coordinate system whose origin is an optional fixed point is set. In other words, mechanical coordinates are set. The axial line of the A axis and the axial line of the B axis as the rotation axes of the machine tool 1 intersect at an intersection point M. Coordinate values of the intersection point M can be represented by (x(t), y(t), z(t)) which is a function of a time point t.

A state in which the tool 8 faces downward in a vertical direction, i.e., a tool axis of the tool 8 is in parallel to the Z axis and the tool tip point 51 faces a negative direction of the Z axis is defined as a reference position (origin) of the A axis and the B axis. Rotation angles of the A axis and the B axis become zero at the reference position.

By using a length ML from the intersection point M to the tool tip point 51, coordinate values (Px(t), Py(t), Pz(t)) of the tool tip point 51 can be represented by the following formula (1) to formula (3).

$$Px(t)=x(t)+ML\times\cos(A(t))\times\sin(B(t)) \qquad (1)$$

$$Py(t)=y(t)+ML\times\sin(A(t)) \qquad (2)$$

$$Pz(t)=z(t)-ML\times\cos(A(t))\times\cos(B(t)) \qquad (3)$$

Px: position of X axis
Py: position of Y axis
Pz: position of Z axis
ML: length from point M to tool tip point
A(t): position of A axis at time point t (rotation angle)
B(t): position of B axis at time point t (rotation angle)

Next, the tangential velocity calculation unit 32 calculates a velocity in a tangential direction of a movement path of a processing point by using the positional information of each drive axis.

Figure 7:
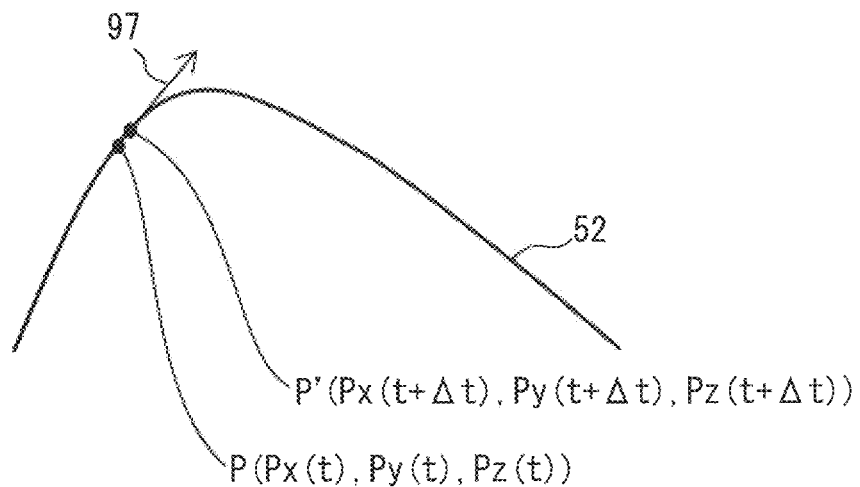
FIG. 7 is a schematic diagram illustrating a velocity in a tangential direction of a movement path.

FIG. 7 shows a schematic diagram of the movement path of the processing point. A position of the processing point corresponds to a position of the tool tip point 51 of the tool 8. The tool tip point 51 moves on a movement path 52 which is determined by the operation program 18. A processing point P and a processing point P' after a short time Δt has passed from the processing point P are depicted. An arrow 97 indicates a velocity in a tangential direction of the processing point P. The velocity in the tangential direction of the movement path 52 of the processing point. P can be calculated on the basis of coordinates of the processing point P and coordinates of the processing point P'. More specifically, a velocity in a direction of each drive axis in the tangential direction of the processing point P can be calculated on the basis of the following formula (4) to formula (6). In addition, a magnitude of the velocity at this time can be calculated by formula (7).

$$Vx(t) = \frac{Px(t+\Delta t) - Px(t)}{\Delta t} \tag{4}$$

$$Vy(t) = \frac{Py(t+\Delta t) - Py(t)}{\Delta t} \tag{5}$$

$$Vz(t) = \frac{Pz(t+\Delta t) - Pz(t)}{\Delta t} \tag{6}$$

$$Vt(t) = \sqrt{Vx(t)^2 + Vy(t)^2 + Vz(t)^2} \tag{7}$$

$Vx(t)$: velocity in X axis direction at time point $t$
$Vy(t)$: velocity in Y axis direction at time point $t$
$Vz(t)$: velocity in Z axis direction at time point $t$
$Vt(t)$: velocity at time point $t$ Referring to FIG. 6, next, at step 83, the movement distance calculation unit 33 calculates a first movement distance of the processing point on the movement path 52 by using the velocity in the tangential direction at the processing point. The first movement distance is calculated on the basis of positional information of each drive axis at a time when processing was actually performed, such as output from the position detectors 11 to 15.

Figure 8:
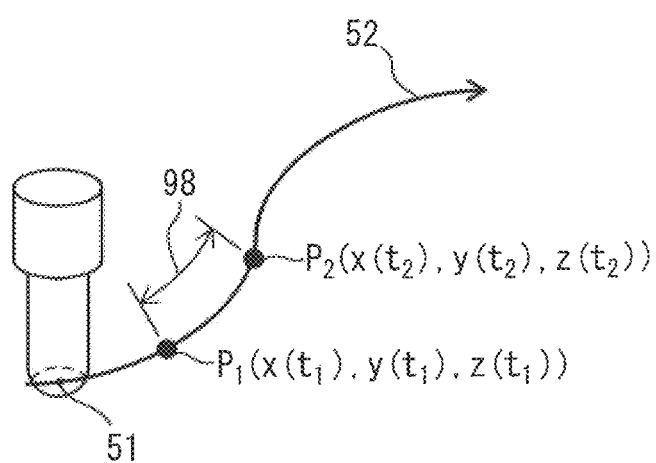
FIG. 8 is a schematic diagram illustrating a first movement distance of a processing point on the movement path.

FIG. 8 shows a schematic diagram of a movement, path which illustrates the first movement distance. The worker can designate, on the movement path 52, a processing point $P_1$ which is a starting point of an analysis and a processing point $P_2$ which is an ending point of the analysis. The processing point $P_1$ and the processing point $P_2$ can be designated by time points. Coordinate values of the processing point $P_1$ and the processing point $P_2$ on each drive axis are specified.

The movement distance calculation unit 33 can calculate a movement distance from the processing point $P_1$ to the processing point $P_2$ by integrating a velocity $Vt(t)$ in the tangential direction of the processing point with time in a section from the processing point $P_1$ to the processing point $P_2$. In the present embodiment, as indicated by an arrow 98, a movement distance along the movement path 52 is referred to as first movement distance. A first movement distance L' corresponds to a length in which the tool tip point 51 has moved on a surface 41 of the workpiece W. The first movement distance L' from a time point $t_1$ to a time point $t_2$ can be calculated by the following formula (8).

$$L' = \int_{t_1}^{t_2} v_t(t)\,dt \tag{8}$$

$$= \int_{t_1}^{t_2} \sqrt{v_x(t)^2 + v_y(t)^2 + v_z(t)^2}\,dt$$

$$= \int_{t_1}^{t_2} \sqrt{\left(\frac{dPx(t)}{dt}\right)^2 + \left(\frac{dPy(t)}{dt}\right)^2 + \left(\frac{dPz(t)}{dt}\right)^2}\,dt$$

$L'$: first movement distance of processing point based on movement path

With reference to FIG. 6, next, at step 84, the streak interval acquisition unit 34 acquires the streak intervals 25 input by the worker from the memory unit 26. In the workpiece W, the section in which streaks to be used for analysis are formed, i.e., the starting point and the ending point of analysis are previously determined by the worker in the present embodiment, the streak interval acquisition unit 34 acquires a plurality of streak intervals 25.

Figure 9:
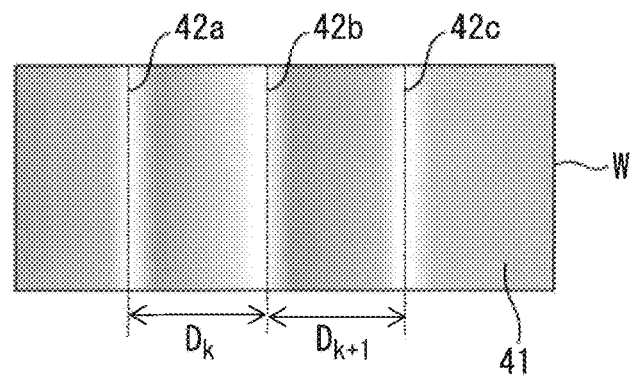
FIG. 9 is a plan view of a workpiece illustrating intervals between streaks.

FIG. 9 shows a plan view of the workpiece which illustrates streak intervals. The worker measures intervals $D_k$ and $D_{k+1}$ between streaks 42a, 42b, and 42c on the basis of a previously determined section to be analyzed. Then, the worker inputs these values to the computation unit 22.

Figure 10:
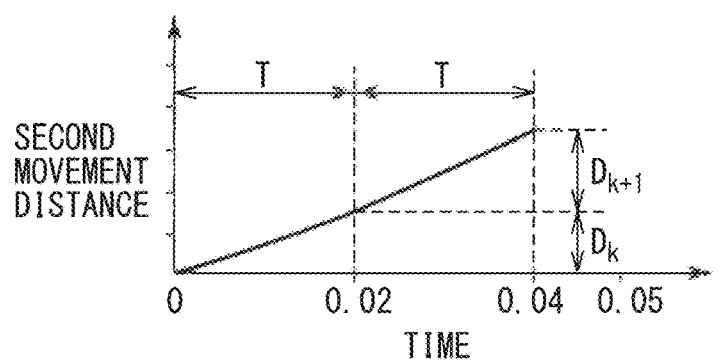
FIG. 10 is a schematic diagram illustrating a second movement distance based on the intervals between streaks.

FIG. 10 shows a graph of the intervals between the streaks with respect to time. Each interval D between the streaks 42 corresponds to a distance in which the processing point moved during the vibration cycle T of the vibration source. In the present embodiment, the movement distance of the processing point is calculated from at least two streak intervals. In the examples shown in FIG. 9 and FIG. 10, the two streak intervals $D_k$ and $D_{k+1}$ are measured. For example, by integrating the intervals $D_k$ and $D_{k+1}$ between the streaks 42, a movement distance between a streak of the starting point and a streak of the ending point which is previously determined can be calculated. In the present embodiment, the movement distance of the processing point based on the intervals between the streaks is referred to as second movement distance.

Referring to FIG. 6, at step 85, the vibration cycle calculation unit 35 can calculate a second movement distance L(t) on the basis of the input streak intervals. The vibration cycle calculation unit. 35 calculates a vibration cycle corresponding to streaks on the basis of the intervals between the streaks on a processed surface and the movement distance of a processing point on a movement path. First will be described a method for calculating a vibration cycle corresponding to streaks on the basis of a cross-correlation function of the first movement distance L'(t) and the second movement distance L(t).

The vibration cycle calculation unit 35 calculates a cross-correlation function $R_r(a, T)$ on the basis of the first movement distance L'(t) and the second movement distance L(t). The cross-correlation function $R_r(a, T)$ can be represented by the following formula (9).

$$R_r(a, T) = \sum_{k=a}^{a+2} L'(T(k-a))L(T(k-a)) \tag{9}$$

$L(t)$: second movement distance of processing point based on streak interval $R_r(a, T)$: cross-correlation function based on $L'(t)$ and $L(t)$ In formula (9), an a-th streak 42 is set as a starting point (a reference). A (a+2)-th streak 42 is an ending point. In the example shown in FIG. 9, a streak 42a is the a-th streak which is the starting point. A streak 42c is the (a+2)-th streak which is the ending point. The cross-correlation function. $R_r(a, T)$ is a function of a variable a and the vibration cycle T.

Formula (9) represents an example of measuring two intervals between the streaks 42, as shown in FIG. 9. Accordingly, a variable k integrates values changing from a to (a+2). A first term of the right side in formula (9) corresponds to a distance of a movement from the starting point to the ending point based on positional information detected by the position detectors. A second term of the right side corresponds to a distance based on the actually measured intervals between streaks.

Next, the vibration cycle calculation unit 35 calculates an auto-correlation function $R_{s1}(a, T)$ of the first movement distance. The auto-correlation function $R_{s1}(a, T)$ of the first movement distance can be calculated by the following formula (10). The auto-correlation function $R_{s1}(a, T)$ of the first movement distance is a function of the variable a.

$$R_{s1}(a, T) = \sum_{k=a}^{a+2} L'(T(k-a))L'(T(k-a)) \quad (10)$$

$R_{s1}(a, T)$: auto-correlation function of $L'(t)$

Next, the vibration cycle calculation unit 35 calculates a correlation ratio $r_1(a, T)$ between the cross-correlation function $R_r(a, T)$ and the auto-correlation function $R_{s1}(a, T)$ of the first movement distance. The correlation ratio $r_1(a, T)$ can be defined as a ratio of the cross-correlation function $R_r(a, T)$ to the auto-correlation function $R_{s1}(a, T)$ of the first movement distance. The correlation ratio $r_1(a, T)$ can be represented as in the following formula (11).

$$r_1(a, T) = \frac{R_r(a, T)}{R_{s1}(a, T)} \quad (11)$$

$r_1(a, T)$: correlation ratio between $R_r$ and $R_{s1}$

Next, the vibration cycle calculation unit 35 calculates the correlation ratio $r_1$ while changing the vibration cycle T and the variable a. As the vibration cycle T and the variable a, values of each previously determined interval in a previously determined range can be used.

Now a correlation between the first movement distance and the second movement distance resulting when the vibration cycle T and the variable a are changed will be explained. The correlation ratio $r_1$ can become larger or smaller than 1.

Figure 11:
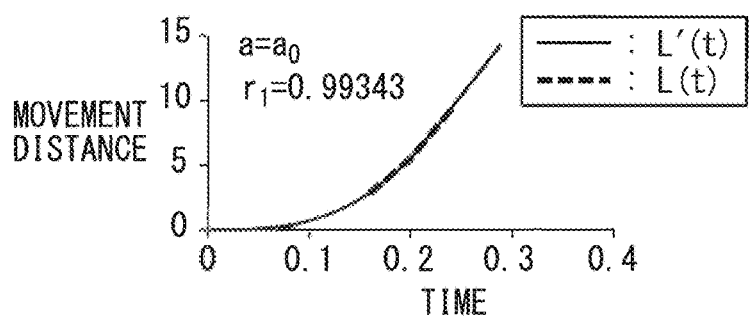
FIG. 11 is a first graph illustrating the first movement distance and the second movement distance with respect to time.
Figure 12:
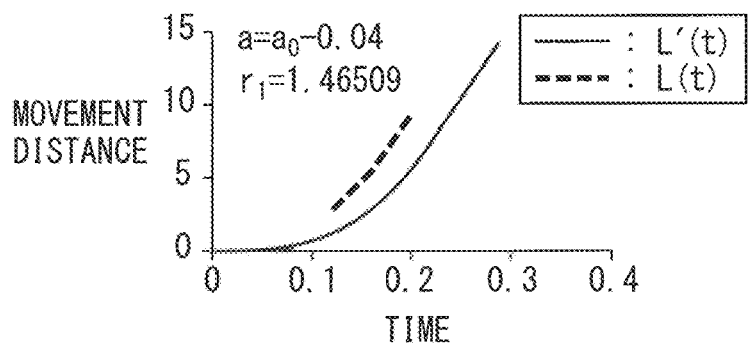
FIG. 12 is a second graph illustrating the first movement distance and the second movement distance with respect to time.
Figure 13:
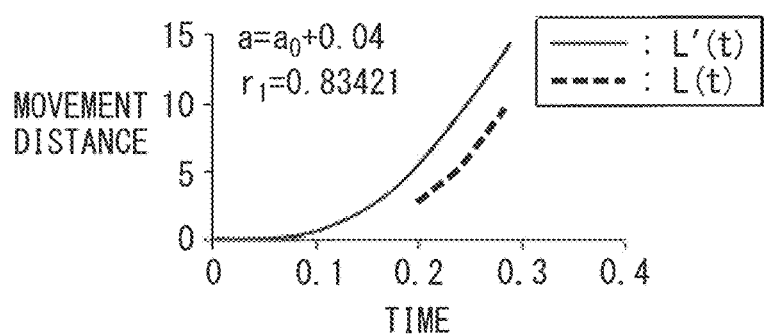
FIG. 13 is a third graph illustrating the first movement distance and the second movement distance with respect to time.

FIG. 11 to FIG. 13 show graphs of the first movement distance and the second movement distance with respect to time in a case in which the variable a is changed. FIG. 11 to FIG. 13 show the graphs where the variable a is changed under conditions of constant vibration cycle. In each of the graphs, the correlation ratio $r_1$ is described. The vibration cycle T is set to a vibration cycle of a vibration source finally obtained by analysis. In the example of the present case, the vibration cycle T is set to 0.04 seconds.

In FIG. 11, the variable a is set to a previously determined $a_0$. The first movement distance $L'(t)$ and the second movement distance $L(t)$ are in an overlapping state. FIG. 12 shows a case in which the value of the variable a has been reduced. In this example, the second movement distance $L(t)$ is moved by −0.04 seconds. When the variable a is changed to the minus side, the graph of the second movement distance $L(t)$ moves to the left side. In contrast to this, referring to FIG. 13, when the variable a is changed to the plus side, the second movement distance $L(t)$ moves to the right side. Thus, changing the variable a moves the second movement distance $L(t)$ in parallel along the time axis. The variable a corresponds to an amount of shift of the graph.

Figure 14:
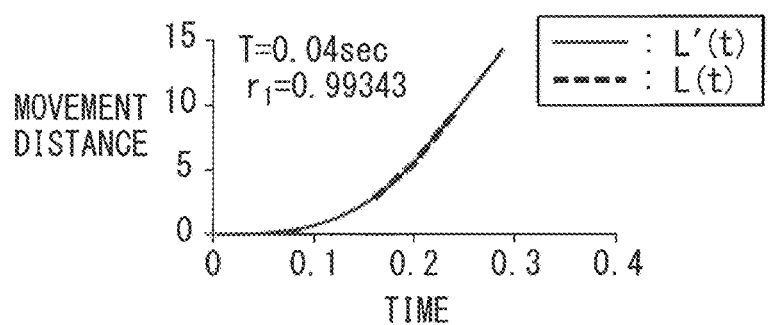
FIG. 14 is a fourth graph illustrating the first movement distance and the second movement distance with respect to time.
Figure 15:
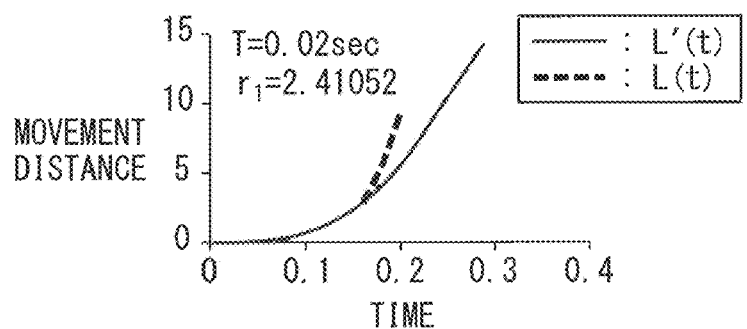
FIG. 15 is a fifth graph illustrating the first movement distance and the second movement distance with respect to time.
Figure 16:
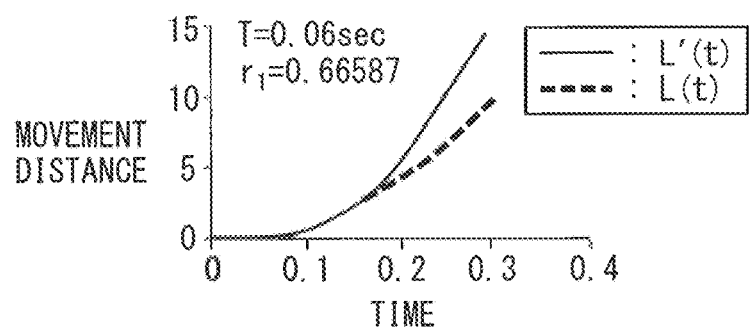
FIG. 16 is a sixth graph illustrating the first movement distance and the second movement distance with respect to time.

FIG. 14 to FIG. 16 show graphs depicting the first movement distance and the second movement distance with respect to time in a case in which the vibration cycle is changed. The variable a is set to $a_0$, as shown in FIG. 11. FIG. 14 is the case in which the vibration cycle T is set to 0.04 seconds which is the vibration cycle of the vibration source, and is the same graph as that of FIG. 11. In FIG. 14, the graph of the second movement distance $L(t)$ coincides with the graph of the first movement distance $L'(t)$.

FIG. 15 shows an example in which the vibration cycle T has been shortened. The gradient of the graph of the second movement distance $L(t)$ increases by shortening the vibration cycle T. Referring to FIG. 10, the entire second movement distance is $(D_k+D_{k+1})$, which is constant. However, when the vibration cycle T is small, the gradient of the graph is large.

FIG. 16 shows a case in which the vibration cycle T has been lengthened. In this case, the gradient of the graph of the second movement distance $L(t)$ decreases by lengthening the vibration cycle T. Referring to FIG. 10, while the entire second movement distance is constant, the vibration cycle T is large. Due to this, the gradient of the graph is small. Referring to the analysis examples of FIG. 14 to FIG. 16, the gradient of the graph of the second movement distance $L(t)$ changes by changing the vibration cycle T.

The following Table 1 shows a list of analysis results of the graphs shown in FIG. 11 to FIG. 16. It can be seen that when the variable a and the vibration cycle T are changed, the correlation ratio $r_1$ changes.

TABLE 1

| a | T [sec] | $r_1(a, T)$ |
|---|---|---|
| $a_0$ | 0.04 | 0.99343 |
| $a_0 - 0.04$ | 0.04 | 1.46509 |
| $a_0 + 0.04$ | 0.04 | 0.83421 |
| $a_0$ | 0.02 | 2.41052 |
| $a_0$ | 0.06 | 0.66587 |

The vibration cycle calculation unit 35 calculates a vibration cycle T and a variable a at which the correlation ratio $r_1$ is closest to 1. In other words, the vibration cycle calculation unit 35 calculates a vibration cycle T and a variable a at which the cross-correlation function $R_r$ is substantially equal to the auto-correlation function $R_{s1}$. The vibration cycle calculation unit 35 calculates the vibration cycle at which the correlation ratio $r_1$ is closest to 1, as a vibration cycle corresponding to streaks. In the above example, the vibration cycle T shown in FIG. 11 and FIG. 14 is calculated as the vibration cycle corresponding to streaks.

Thus, the vibration analysis device of the present embodiment has the function of analyzing streaks on a processed surface due to vibration with the constant cycle. Then, even in cases in which the velocity of a processing point is not constant and streak intervals are not even, a vibration cycle can be calculated on the basis of the streak intervals and the movement distance of the processing point. More specifically, the vibration analysis device 21 can calculate the vibration cycle T of the tool with respect to the workpiece even when there is a section in which the relative velocity of the tool 8 with respect to the workpiece W changes. Alternatively, the vibration analysis device 21 can calculate a vibration frequency corresponding to the streaks on the basis of the vibration cycle T.

Meanwhile, a device vibrating at the same frequency as the vibration frequency calculated by the vibration analysis device 21 is a vibration source. The worker can identify a vibration source which is the cause of occurrence of streaks by using the calculated vibration cycle and vibration frequency. Then, the worker can perform appropriate processing against the vibration source so that no vibration occurs or can perform an inspection of the vibration source. For example, in a case in which there is something abnormal in the fan motor of the inverter, processing for replacing the fan motor can be performed.

In the above embodiment, the vibration frequency corresponding to the streaks is calculated or the basis of the cross-correlation function of the first movement distance and the second movement distance. The method for calculating a vibration cycle by using a cross-correlation function is not limited to this form, and other methods can be employed.

In a second vibration analysis device of the present embodiment, the vibration cycle calculation unit 35 calculates a cross-correlation function between the first movement distance and the second movement distance by the above-described control. Additionally, the vibration cycle calculation unit 35 calculates an auto-correlation function of the second movement distance. Then, the vibration cycle calculation unit 35 calculates a value of a normalized cross-correlation function on the basis of the auto-correlation function of the first movement distance, the auto-correlation of the second movement distance, and the cross-correlation function. An auto-correlation function $R_{s2}$ of the second movement distance L(t) can be calculated by the following formula (12).

$$R_{s2}(a, T) = \sum_{k=a}^{a+2} L(T(k-a))L(T(k-a)) \quad (12)$$

$R_{s2}(a, T)$: auto-correlation function of $L(t)$

Then, a normalized cross-correlation function $r_2$ can be calculated by the following formula (13). The normalized cross-correlation function $r_2$ is a value equal to or larger than 1. The normalized cross-correlation function is a value obtained by dividing the cross-correlation function by a square root of the auto-correlation function of the first movement distance and a square root of the auto-correlation function of the second movement distance.

$$r_2(a, T) = \frac{R_r(a, T)}{\sqrt{R_{s1}(a, T)} \cdot \sqrt{R_{s2}(a, T)}} \quad (13)$$

$r_2(a, T)$: normalized cross-correlation function

The following Table 2 shows an analysis example of a normalized cross-correlation function in a case in which the variable a is changed and a case in which the vibration cycle T is changed in the second vibration analysis device. The variable a and the vibration cycle T can be changed at each previously determined interval in a previously determined section. It can be seen that when the variable a and the vibration cycle T are changed, the normalized cross-correlation function $r_2$ changes. In this example, when the variable a is $a_0$ and additionally the vibration cycle T is 0.04, the graph of the first movement distance and the graph of the second movement distance best coincide. At this time, the normalized cross-correlation function $r_2$ is found to be closest to 1.

TABLE 2

| a | T [sec] | $r_2$ (a, T) |
|---|---|---|
| $a_0$ | 0.04 | 0.99999 |
| $a_0 - 0.04$ | 0.04 | 0.99773 |
| $a_0 + 0.04$ | 0.04 | 0.98839 |
| $a_0$ | 0.02 | 0.99807 |
| $a_0$ | 0.06 | 0.99515 |

In the second vibration analysis device, the vibration cycle calculation unit 35 changes the vibration cycle T and the variable a in the previously determined section. The vibration cycle calculation unit 35 changes the vibration cycle T and the variable a at each previously determined interval and calculates the normalized cross-correlation function $r_2$. The vibration cycle calculation unit 35 calculates a vibration cycle T and a variable a at which the normalized cross-correlation function $r_2$ is closest to 1. Then, the vibration cycle calculation unit 35 can set the vibration cycle T at this time as a vibration cycle corresponding to streaks.

In this way, the vibration cycle calculation unit 35 according to the present embodiment can calculate the vibration cycle T so that the correlation between the first movement distance of the processing point and the second movement distance of the processing point is high in the previously determined section. In addition, the display unit 24 can display the vibration cycle T calculated by the vibration cycle calculation unit 35.

Next, a third vibration analysis device of the present embodiment will be described. In the third vibration analysis device, the vibration cycle calculation unit 35 calculates a vibration cycle at which a difference between the first movement distance and the second movement distance is smallest, as a vibration cycle corresponding to streaks. The vibration cycle calculation unit 35 calculates an integrated value of a square of the difference between the first movement distance and the second movement distance, and can calculate a vibration cycle at which the integrated value is smallest. In other words, the vibration cycle calculation unit 35 can set a variable a and a vibration cycle T by a least-square method using the variable a and the vibration cycle T as variables. Then, the vibration cycle calculation unit 35 can calculate the vibration cycle as the vibration cycle T corresponding to streaks. An integrated value S(a, T) of the square of the difference between the first movement distance L'(t) and the second movement distance L(t) is as in the following formula (14). The integrated value S(a, T) is a function of the variable a and the vibration cycle T.

$$S(a, T) = \sum_{k=a}^{a+2} \{L'(T(k-a)) - L(T(k-a))\}^2 \quad (14)$$

$S(a, T)$: integrated value

Figure 17:
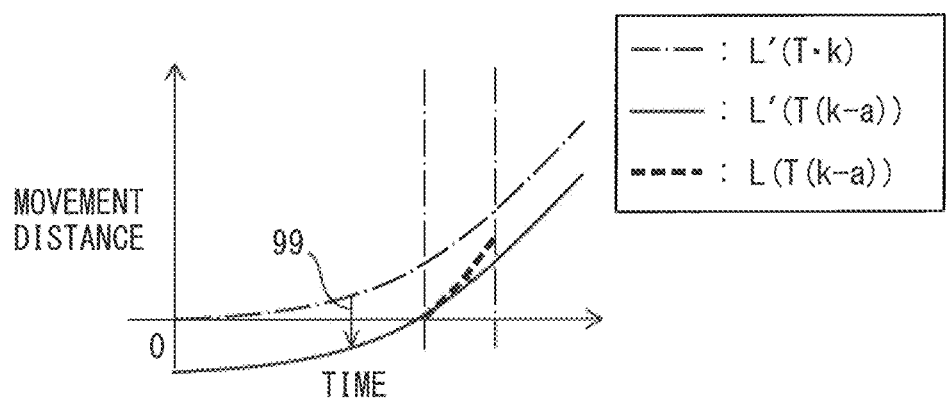
FIG. 17 is a graph illustrating a calculation method for a least-square method.

FIG. 17 shows a graph illustrating a least-square method formula. The lateral axis represents time, and the vertical axis represents movement distance. As described above, changing the variable a can move the second movement distance. Changing the vibration cycle T can change the gradient of the second movement distance. Then, in formula (14), the difference with the second movement distance L(t) can be calculated in a state in which the first movement distance L'(t) has been moved, as indicated by an arrow 99.

The following Table 3 shows an analysis example of the integrated value S in a case in which the variable a is changed and a case in which the vibration cycle T is changed. The variable a and the vibration cycle T can be changed in a previously determined section at each previously determined interval. When the variable a and the vibration cycle T are changed, the integrated value S is found to change. Then, when the variable a is $a_0$ and additionally the vibration cycle T is 0.04, the first movement distance and the second movement distance best coincide. At this time, the integrated value S is found to be smallest.

TABLE 3

| a | T [sec] | S(a, T) |
|---|---|---|
| $a_0$ | 0.04 | 0.23667 |
| $a_0 - 0.04$ | 0.04 | 7.99240 |
| $a_0 + 0.04$ | 0.04 | 10.8096 |
| $a_0$ | 0.02 | 5.23030 |
| $a_0$ | 0.06 | 5.38348 |

The vibration cycle calculation unit 35 can calculate a value by subtracting the second movement distance from the first movement distance on the basis of formula (14). Then, the vibration cycle calculation unit 35 can calculate a vibration cycle at which the integrated value S obtained by squaring the value is smallest, and can calculate the vibration cycle as a vibration cycle corresponding to streaks.

In this way, the vibration cycle T can be calculated on the basis of the integrated value of the square of the difference between the first movement distance of the processing point and the second movement distance of the processing point. In the third vibration analysis device also, the display unit 24 can display the vibration cycle T calculated by the vibration cycle calculation unit 35.

The vibration analysis device of the present embodiment is suitable to the processing in which the relative velocity of the tool with respect to a workpiece changes during a period in which the workpiece is processed, and also can calculate the vibration cycle by the same method even when the relative velocity of the tool with respect to a workpiece is constant.

According to the present invention, there can be provided the vibration analysis device which calculates the cycle of vibration of the tool with respect to a workpiece.

In each control described above, the sequential order of the steps can be changed as appropriate in a range in which the functions and effects are not changed. The above embodiments can be combined as appropriate. In each of the above-described drawings, the same or equivalent parts are denoted by the same reference numerals. In addition, the above embodiments are illustrative and do not limit the invention. Additionally, the embodiments include changes to the embodiments set forth in the claims.

The invention claimed is:

1. A system comprising:
   a controller having a processor configured to control a machine tool to move along a drive axis; and
   a vibration analysis device which calculates a vibration cycle at which a tool vibrates with respect to a workpiece during a period in which the workpiece is processed by the machine tool controlled by the controller, the vibration analysis device comprising:
   a processor configured to:
     acquire positional information of the drive axis in time series,
     calculate a velocity in a tangential direction of a movement path of a processing point by using the positional information,
     calculate a first movement distance of the processing point on the movement path by using the velocity in the tangential direction,
     acquire a previously measured interval between streaks on the workpiece,
     calculate a vibration cycle corresponding to the streaks on the basis of the interval between the streaks and the first movement distance of the processing point,
     calculate a second movement distance of the processing point on the basis of at least two of the intervals between the streaks,
     calculate a cross-correlation function of the first movement distance and the second movement distance, and
     calculate the vibration cycle corresponding to the streaks on the basis of the cross-correlation function.

2. The vibration analysis device according to claim 1, wherein the processor is further configured to calculate a correlation ratio between the cross-correlation function and an auto-correlation function of the first movement distance, and calculate the vibration cycle at which the correlation ratio is closest to 1, as the vibration cycle corresponding to the streaks.

3. The vibration analysis device according to claim 1, wherein the processor is further configured to calculate a value of a normalized cross-correlation function on the basis of an auto-correlation function of the first movement distance, an auto-correlation function of the second movement distance, and the cross-correlation function, and calculate the vibration cycle at which the value of the normalized cross-correlation function is closest to 1, as the vibration cycle corresponding to the streaks.

4. A system comprising:
   a controller having a processor configured to control a machine tool to move along a drive axis; and
   a vibration analysis device which calculates a vibration cycle at which a tool vibrates with respect to a workpiece during a period in which the workpiece is processed by the machine tool controlled by the controller, the vibration analysis device comprising:
   a processor configured to:
     acquire positional information of a drive axis in time series,
     calculate a velocity in a tangential direction of a movement path of a processing point by using the positional information,
     calculate a first movement distance of the processing point on the movement path by using the velocity in the tangential direction,
     acquire a previously measured interval between streaks on the workpiece, and
     calculate a vibration cycle corresponding to the streaks on the basis of the interval between the streaks and the first movement distance of the processing point, wherein the processor is further configured to calculate a second movement distance of the processing point on the basis of at least two of the intervals between the streaks, and calculate the vibration cycle at which a difference between the first movement distance and the second movement distance is smallest, as the vibration cycle corresponding to the streaks.

5. The vibration analysis device according to claim 4, wherein the processor is further configured to calculate an integrated value of a square of the difference between the first movement distance and the second movement distance at a plurality of points, and calculate the vibration cycle at which the integrated value is smallest, as the vibration cycle corresponding to the streaks.

* * * * *